US009068998B2

(12) United States Patent
Lunding

(10) Patent No.: US 9,068,998 B2
(45) Date of Patent: Jun. 30, 2015

(54) REFERENCE SOLUTION

(75) Inventor: Gitte Lunding, Broenshoej (DK)

(73) Assignee: Radiometer Medical ApS, Bronshoj (DK)

( * ) Notice: Subject to any disclaimer, the term of this patent is extended or adjusted under 35 U.S.C. 154(b) by 924 days.

(21) Appl. No.: 12/140,892

(22) Filed: Jun. 17, 2008

(65) Prior Publication Data

US 2008/0254542 A1 Oct. 16, 2008

Related U.S. Application Data

(62) Division of application No. 10/998,009, filed on Nov. 29, 2004, now abandoned.

(60) Provisional application No. 60/554,417, filed on Mar. 19, 2004.

(30) Foreign Application Priority Data

Nov. 28, 2003 (DK) ................................. 2003 01758

(51) Int. Cl.
*G01N 33/70* (2006.01)
*C12Q 1/34* (2006.01)
*C12Q 1/00* (2006.01)
*G01N 33/96* (2006.01)

(52) U.S. Cl.
CPC ............... *G01N 33/96* (2013.01); *Y10T 436/10* (2013.01); *C12Q 1/34* (2013.01); *G01N 2333/986* (2013.01); *G01N 33/70* (2013.01); *C12Q 1/001* (2013.01)

(58) Field of Classification Search
None
See application file for complete search history.

(56) References Cited

U.S. PATENT DOCUMENTS

| | | | |
|---|---|---|---|
| 3,806,420 A * | 4/1974 | Holz et al. ..................... | 435/231 |
| 3,907,644 A | 9/1975 | Mollering et al. | |
| 4,189,401 A | 2/1980 | Louderback et al. | |
| 4,215,197 A | 7/1980 | Tarbutton | |
| 4,446,231 A | 5/1984 | Self | |
| 4,780,191 A | 10/1988 | Romette et al. | |
| 4,812,220 A | 3/1989 | Iida et al. | |
| 5,047,329 A | 9/1991 | Suzuki | |
| 6,051,389 A | 4/2000 | Ahl et al. | |
| 6,080,553 A | 6/2000 | Sogabe et al. | |
| 6,242,207 B1 | 6/2001 | Douglas et al. | |
| 6,451,607 B1 | 9/2002 | Lawrence et al. | |
| 6,501,549 B1 | 12/2002 | Andrade et al. | |
| RE38,687 E | 1/2005 | Sogabe et al. | |
| RE39,352 E | 10/2006 | Sogabe et al. | |
| 7,371,314 B2 * | 5/2008 | Schaffar et al. ............... | 205/792 |

FOREIGN PATENT DOCUMENTS

| | | |
|---|---|---|
| EP | 0 291 321 A2 | 11/1988 |
| GB | 2185318 A | 7/1987 |
| WO | WO 02/14533 A2 | 2/2002 |
| WO | WO 02014533 A2 * | 7/2002 |
| WO | WO 2005/052596 A1 | 6/2005 |

OTHER PUBLICATIONS

Shin, J.H. et al "A Planar Amperometric Creatinine Biosensor Employing an Insoluble Oxidizing Agent for Removing Redox-Active Interferences" Anal. Chem., 2001, 73(24), pp. 5965-5971.*
Graham, Edgar and Shiver, H. E. The Equilibrium Between Creatine and Creatinine, in Aqueous Solution. The Effect of Hydrogen Ion, JACS, Apr. 4, 1925, 47(4), pp. 1179-1188.*
Scheller, Frieder and Schubert, Florian, "Metabolism Sensors: Multienzyme Electrodes for Creatinine and Creatine" Biosensors, Nov. 21, 1991, Chapter 3 §3.2.1.8, pp. 209-210.*
Killard A, Smyth M. "Creatinine biosensors: principles and design" Trends Biotechnol, Oct. 1, 2000, 18(10), pp. 433-437.*
Cannan RK, Shore A. "CXV. The creatine-creatinine equilibrium. The apparent dissociation constants of creatine and creatinine" Biochem J, 1928, 22, pp. 920-929.*
Skurup, Anne; Kristensen, Tina; Wennecke, Gitte "New Creatinine Sensor for Point-of-Care Testing of Creatinine Meets the National Kidney Disease Education Program Guidelines" Clin Chem Lab Med, 2008, 46(1), pp. 3-8.*
Edgar, G. and Shiver, H.E., "The Equilibrium Between Creatine and Creatinine, in Aqueous Solution. The Effect of Hydrogen Ion" J. Am. Chem. Soc., Apr. 1925, 47 (4), pp. 1179-1188.*
Botre et al. (1990) Determination of Carbonic Anhydrase Activity by a $pCO_2$ Sensor, Anal. Biochem., 185(2):254-264.
Lakshmi et al. (1991) Regional Distribution of 11β-Hydroxysteroid Dehydrogenase in Rat Brain, Endocrinology, 128(4):1741-1748.
Perakis et al. (1984) Kinetic Approach for the Enzymic Determination of Creatinine, Clin. Chem. , 30(11):1792-1796.
Rikitake et al. (1979) Creatinine Amidohydrolase (Creatininase) from *Pseudomonas putida*: Purification and Some Properties, J. Biochem. 86(4): 1109-1117.

* cited by examiner

*Primary Examiner* — Jon P Weber
*Assistant Examiner* — Aaron J Kosar
(74) *Attorney, Agent, or Firm* — Finnegan, Henderson, Farabow, Garrett & Dunner

(57) ABSTRACT

A reference solution is provided, which comprises, in a liquid phase, at least one of a first compound and a second compound which are mutually convertible into each other, and at least one catalyst, which catalyzes the conversion between the first compound and the second compound.

14 Claims, 2 Drawing Sheets

REFERENCE SOLUTION

RELATED APPLICATIONS

The present application is a divisional application of U.S. application Ser. No. 10/998,009, filed Nov. 29, 2004, now abandoned which claims the benefit of U.S. Provisional Application 60/554,417, filed Mar. 19, 2004, and Danish Patent Application No. PA200301758, filed Nov. 28, 2003, each of which is herein incorporated by reference in its entirety.

FIELD OF THE INVENTION

The present invention relates to a reference solution, a kit for providing a container holding the reference solution, a method of operating the kit, a container holding the reference solution, a method of preparing the reference solution and use of the reference solution.

BACKGROUND OF THE INVENTION

Sensors for measuring parameters in a test fluid are widely used in various fields of chemistry, biology and physiology.

In order to assure that sensor measurements are accurate, the sensor should be regularly calibrated. Calibrating the sensor typically involves determining experimentally the correspondence between a sensor response and a predetermined parameter value of a reference material, and adjusting the sensor in accordance therewith.

The quality of the sensor performance should also be controlled on a regular basis to verify experimentally that the sensor measurements are accurate. This is usually done by comparing a measured parameter value of a reference material to an acceptance range of the same reference material.

Reference materials for calibration and quality control routines comprise compounds, which represent the parameter in question. The parameter may be a physical parameter, such as viscosity, density, pressure and conductivity, or a chemical parameter, such as pH or the concentration of gasses, electrolytes or metabolites of a physiological liquid, like blood. The reference materials should represent the parameter precisely and steadily over their lifetime. Therefore, reference materials may comprise compounds in concentrations which are stable over time, e.g., compounds in chemical equilibrium, and they should be prepared and stored under closely controlled conditions to assure fulfillment of their specifications.

In some cases such controlled conditions of preparation and storage may not suffice to fulfill the specifications. This may be the case with a reference solution comprising two compounds which exist in equilibrium and which are mutually convertible into each other. The equilibrium between such two compounds may be temperature dependent. If so, then, any temperature change is likely to gradually change the chemical composition of the reference solution.

One such reference solution may include a dissolved gas, in which the gas may be distributed between a gaseous phase in a container headspace and a dissolved phase in the solution. With such a system, the equilibrium distribution of gas between the two phases may be temperature dependent. Thus, if the solution is stored at a temperature different from the operating temperature, the distribution of gas may be different from the equilibrium distribution at the operating temperature. The reference solution may therefore need long term conditioning before use in order to establish a state of equilibrium between the two phases corresponding to the operating temperature.

Another type of two-phase reference solution is a system comprising a sparingly soluble compound, which may exist partly as solute and partly as solid phase. The distribution between these two phases may be temperature dependent, and the solution may also need long term conditioning before use in order to establish a state of equilibrium at the operating temperature.

Still other reference solutions involve chemical reactions, in which two or more compounds exist in equilibrium. Examples include the systems of glutamine and glutamic acid/glutamate and of carbon dioxide and carbonic acid, as well as the mutarotational system of $\alpha$-D-glucose and $\beta$-D-glucose. Reference solutions comprising these compounds may require conditioning for days, months or even years before use in order to establish a state of equilibrium at the operating temperature.

Yet another example of a system comprising two compounds in equilibrium is the system of creatinine and creatine. As with the examples above, long term conditioning may be needed as the equilibrium between these two compounds is established only over a period of months or years.

International Published Patent Application WO 02/14533 to Roche Diagnostics GmbH discloses a method of calibrating a creatinine sensor. According to this method, two calibration solutions are used. The first calibration solution is an acidic solution of creatinine, which is first neutralized before being used for calibration. The neutralization step, however, makes this procedure inconvenient for daily operation. The second solution is a solution of creatinine and creatine at equilibrium concentrations corresponding to a specific temperature. However, to avoid compositional changes, such a solution should either be prepared immediately before use or kept at that specific temperature, both of which are impractical in daily use.

Thus, despite the hitherto proposed reference solutions for detection of mutually convertible compounds, there is still a need for a reference solution which does not require extended conditioning and/or instant preparation. Accordingly, it is an object of the present invention to provide such a reference solution.

SUMMARY OF THE INVENTION

In one aspect of the invention, a reference solution is provided which comprises, in a liquid phase, at least one of a first compound and a second compound, which are mutually convertible into each other, and at least one catalyst, which catalyzes the conversion between the first and second compounds.

Another aspect of the invention is a kit for providing a container holding the reference solution of the invention, comprising a container holding the reference solution described above, comprising at least a first compartment and a second separate compartment; a liquid first phase contained in the first compartment; and a second phase contained in the second separate compartment, said second phase comprising the at least one of a first compound and a second compound and the at least one catalyst.

In another aspect of the invention, a method of operating the kit is provided.

In another aspect of the invention, a container holding the reference solution is provided.

In another aspect of the invention, a method of preparing the reference solution of the invention is provided, comprising the steps of adding to a liquid phase at least one of a first compound and a second compound; and at least one catalyst; and determining, before or after addition of the at least one catalyst, the equilibrium concentrations of the first compound and the second compound for a selected temperature.

In another aspect of the invention, use of the reference solution of the invention for calibration or quality control of a sensor is provided.

FIGURES

DETAILED DESCRIPTION

Figure 1:
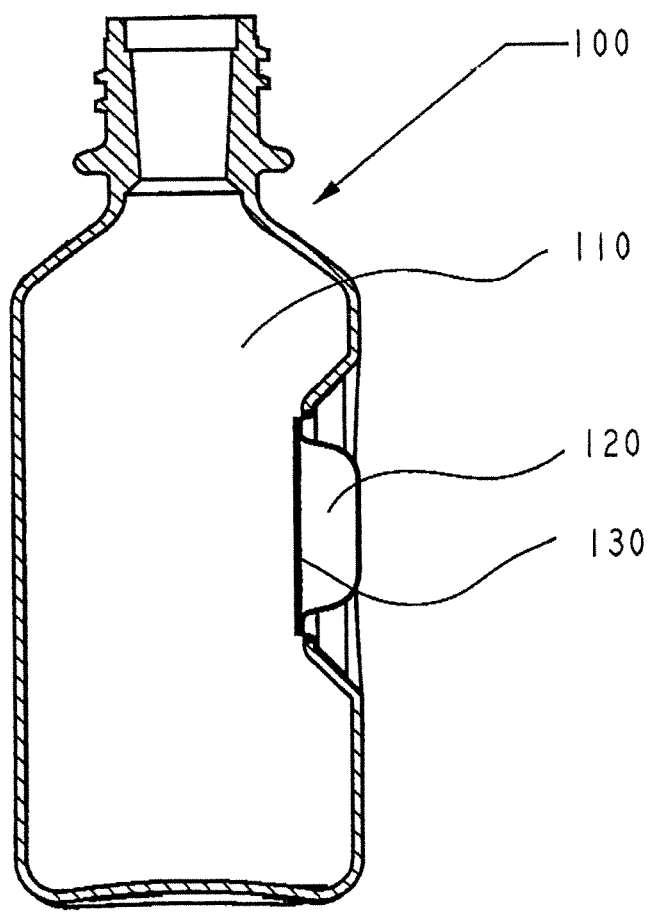
FIG. 1 shows a kit for providing a container holding a reference solution according to an exemplary embodiment of the invention.

As used herein, the term "reference solution" means a solution for calibration and/or quality control of sensors. Thus, the reference solution may be used for calibration of a sensor for which it is intended, and or it may be used for quality control of the sensor.

The term "liquid phase" means the solvent of the reference solution, or e.g., a buffer solution, or a solution of one or more compounds other than the mutually convertible compounds for which it may also serve as a reference solution.

The term "compound" means a chemical substance or a mixture of chemical substances. According to the invention, the species to be determined by the sensor may in fact be one of the first and the second compounds of the reference solution, or it may be a reaction product derived from the first and/or the second compound(s).

The term "catalyst" may refer to a single catalyst, which catalyzes the conversion reaction in both directions, or to a combination of, e.g., two catalysts, one of which catalyzes the conversion reaction in one direction and the other of which catalyzes the conversion reaction in the opposite direction.

As used herein, the term "mutually convertible" means that the compounds of the reference solution, may, by chemical reaction in either direction, be transformed into one another.

As further used herein, the term "equilibrium concentrations" means the concentrations of the first and the second compounds in the reference solution when the reference solution is in a state of equilibrium at a given temperature, i.e., when there is no net conversion between the first and the second compounds at the given temperature.

The term "separate compartment" means a compartment of the described container which is adapted to hold a phase in such a way, that it is not in contact with any other phases held in any other compartments of the container.

As used herein, the term "computing the equilibrium concentration therefrom" means calculating, from the total concentration of the first and the second compound, the equilibrium concentration of each compound at a given temperature. The calculation may be based on a predetermined algorithm that includes equilibrium data, e.g., equilibrium constants as a function of temperature.

As used herein, the term "computing the equilibrium concentration of the other compound therefrom" means calculating from the equilibrium concentration of the first compound the equilibrium concentration of the second compound at a given temperature. The calculation may be based on a predetermined algorithm that includes equilibrium data, e.g., equilibrium constants as a function of temperature.

As used herein, the term "predetermined amount(s)" means that the first and/or second compound(s) are added in (an) amount(s), corresponding to (a) specific concentration(s) of the compound(s), determined prior to addition to the liquid phase, by e.g., a weighing procedure. Thus, the amounts added may correspond to the equilibrium concentrations of the first and second compounds at the operating temperature of the reference solution, i.e., the reference solution as prepared may be in a state of equilibrium, or it may correspond to non-equilibrium concentrations. In the latter case the equilibrium concentration may be computed as defined above, i.e., based on an algorithm that includes equilibrium data, e.g., equilibrium constants as a function of temperature.

As used herein, the term "sensor" means any kind of device, which is capable of selectively interacting with the chemical species of interest, thereby producing a well-defined and measurable response which is a function of a desired characteristic of that particular chemical species. Relevant types of sensors are those adapted to determine e.g., any of the previously mentioned parameters, for example potentiometric sensors, where the response appears in the form of an electrical potential; amperometric sensors, where the response appears in the form of an electrical current; optical sensors; piezoelectric sensors; thermometric sensors; pressure-change sensors; acoustic sensors or any combination thereof.

As used herein, the term "conditioning" means allowing the reference solution to adjust to a given temperature.

Compared to traditional reference solutions which are limited to two mutually convertible compounds, the reference solution according to the invention also contains a catalyst, which catalyzes the conversion between the first compound and the second compound. The catalyst accelerates the conversion between the first and the second compounds, ensuring the fast establishment of a state of equilibrium between the two compounds at the operating temperature of the reference solution. Thus, the reference solution of the present invention eliminates the need for extended periods of conditioning and instant preparation. After a reduced period of conditioning, the reference solution of the present invention is in a state of equilibrium, and its chemical composition can be determined entirely from its temperature. In this way the reference solution of the present invention may be easily provided as a ready-to-use solution, e.g., as provided in sealed ampoules.

Prior to use, the reference solution may comprise only one compound of the first and the second compounds. Thus, even if the solution is prepared from one compound only, i.e., from the first compound only or from the second compound only, the state of equilibrium between the first and the second compounds is quickly established once the catalyst is present and the operating temperature of the reference solution is reached.

The first and second compounds should be mutually convertible into each other. According to the invention, the first and the second compounds may be the same species in two different phases, e.g., gaseous and dissolved carbon dioxide.

The reference solution may comprise one or more catalysts, which alone or in combination, catalyze the conversion reaction in both directions. The amount of catalyst needed for catalyzing the conversion reaction depends on the nature of the system. Catalyst degradation, which results in some loss of catalytic activity may occur during the lifetime of the reference solution. Therefore, the catalyst concentration should be sufficient to catalyze the conversion reaction for the complete lifetime of the reference solution.

The catalyst may be an enzyme, i.e., a catalyzing protein, or a coenzyme necessary for the action of an enzyme. Alternatively, the catalyst may be another catalyzing compound, which mimics the effect of an enzyme, e.g., an enzyme-mimicking polymer.

One type of conversion reaction that may be used in the invention is a hydrolysis reaction. Hydrolysis reactions may be catalyzed by e.g., enzymes that are hydrolases. Thus, in one embodiment of the invention, the catalyst is a hydrolase enzyme.

Amides and esters represent a group of compounds that may be used in the invention. Thus, in another embodiment of the invention, the first compound is an amide or an ester.

Hydrolysis reactions and conversion reactions involving amides or esters are both characterized by their rather low reactions rates, when compared to more practical periods of conditioning. During long term storage, however, such reference solutions may still be subject to significant compositional changes. In the absence of a catalyst, there is no establishment of a state of equilibrium at a chosen operating temperature within practical time limits. The addition of a catalyst to such reference solutions may reduce the conditioning period by orders of magnitude.

In reference solutions comprising creatinine-creatine as the first and second compounds, the catalyst may be the enzyme creatinine amidohydrolase, EC 3.5.2.10. In this system, the parameter of interest may be creatinine, creatine or a parameter derived therefrom.

In reference solutions comprising glutamine-glutamic acid/glutamate as the first and second compounds, the catalyst may be one or more of the enzymes glutaminase, EC 3.5.1.2, and glutamine synthetase, EC 6.3.1.2. In this system, the parameters of interest may be glutamine, glutamic acid or glutamate or a parameter derived therefrom.

In reference solutions comprising carbon dioxide and carbonic acid as the first and second compounds, the catalyst may be the enzyme carbonic anhydrase, EC 4.2.1.1. In this system, the parameters of interest may be carbon dioxide, carbonic acid or a parameter derived therefrom.

In reference solutions comprising the mutarotational system of $\alpha$-D-glucose and $\beta$-D-glucose as the first and second compounds, the catalyst may be the enzyme mutarotase, also referred to as aldose 1-epimerase, EC 5.1.3.3. In this system, the parameters of interest may be either of the two glucose species or a parameter derived therefrom.

The reference solution may comprise additional compounds beyond the first and second mutually convertible compounds and the catalyst. As such, the reference solution may be used for calibration and/or quality control of one or more additional sensors for analysis of one or more additional parameters. Thus, in addition to being a reference solution for a sensor for analysis of the first and/or second compound(s) of e.g. blood, or of a parameter derived therefrom, the reference solution may also be used for one or more additional blood parameters such as $pO_2$, $pCO_2$, pH, sodium, potassium, calcium, chloride, glucose, lactate, urea, bilirubin, hemoglobin or any derivative of hemoglobin. Such a reference solution may be used for calibration and/or quality control of a plurality of sensors, thereby reducing the number of required individual reference solutions and saving costs.

A kit for providing a container holding the reference solution of the invention may comprise a container with at least a first compartment and a second separate compartment, a liquid first phase being contained in the first compartment, and a second phase being contained in the second separate compartment, the second phase comprising at least one of the first compound, the second compound and the catalyst of the reference solution.

The kit of the invention allows for separated storage of the phases involved in the reference solution. With the kit, the reference solution may be prepared by combining the separated phases immediately before use, thus extending the lifetime of the catalyst through dry storage.

A first compartment may be used to hold e.g., a buffer solution, and one or more of the first and second compounds, and the catalyst may be held in a second separate compartment. Alternatively, a first compartment may be used to hold a solution of e.g. the first and/or the second compound(s), and the catalyst may be held in a second separate compartment; or a first compartment may be used to hold the catalyst in solution, and the first and/or the second compound(s) may be held in a second separate compartment.

The first and the second compartments may have any shape which effectively separates the phases held in the two compartments. Thus, the second compartment may be separated from the first compartment by means of a thin wall which may be broken or displaced upon the exertion of manual pressure on the outer surface of the second compartment, e.g., in terms of a blister pack as used in tablet packages. Alternatively, the second compartment may be adapted to receive e.g., a plunger, which has a pointed end. When the plunger is depressed, the end penetrates a thin wall of the second compartment to form a fluid conduit from the second compartment into the first compartment, thus delivering the phase from the second compartment into the first compartment.

The container may have a third separate compartment, such that at least one of the first and the second compounds is contained in the second compartment and the catalyst is contained in the third compartment. According to this embodiment of the invention, the first and/or the second compound(s) are separated from the catalyst during storage. The first compartment may be used to hold a buffer of the reference solution, while the first and/or the second compound(s) may be held in the second separate compartment and the catalyst may be held in the third separate compartment.

The container may comprise additional separate compartments beyond the three compartments described, e.g., holding compounds other than the mutually convertible first and second compounds and the catalyst.

In operating the kit, the second phase may be transferred to the first phase by providing fluid communication between the compartments. Thus, according to this method, the second phase containing at least one of the first and second compounds and the catalyst is transferred to the liquid first phase to prepare the reference solution.

A container holding the reference solution may comprise a first compartment and a second separate compartment as described above. The container may be a two-compartment syringe as is known in the art, or it may be a two-compartment ampoule.

The reference solution of the present invention may as well be provided in one-compartment containers, e.g., one-compartment ampoules, in which all of the at least one of the first compound and the second compound, and the at least one catalyst are mixed in the liquid phase.

A method of preparing the reference solution of the invention may comprise the steps of adding to a liquid phase (a) at least one of the first and the second compounds, and (b) at least one catalyst, and, before or after addition of the at least one catalyst, determining the equilibrium concentrations of the first and second compounds for a selected temperature. Steps (a) and (b) may be performed in any order, i.e., step (a) followed by step (b), or step (b) followed by step (a).

The step of determining the equilibrium concentrations of the first and second compounds may comprise (a) measuring the total concentration of the first and second compounds, and (b) computing the equilibrium concentrations therefrom.

Determination of the total concentration of the first and the second compounds is independent of whether or not the solution is in a state of equilibrium. Any net conversion, e.g., from the first compound to the second compound, will not influence the total concentration of the two compounds, as an increase in the concentration of the second compound will be counterbalanced by a corresponding decrease in the concentration of the first compound.

In an embodiment of the invention, the step of determining the equilibrium concentrations comprises (a) measuring the concentrations of each of the first and second compounds, and (b) computing the equilibrium concentrations therefrom.

In another embodiment of the invention, the step of determining the equilibrium concentrations comprises (a) allowing establishment of the equilibrium concentrations of the first and second compounds after addition of the catalyst, (b) measuring the equilibrium concentration of one of the compounds, and (c) computing the equilibrium concentration of the other compound therefrom. In this embodiment of the invention, the reference solution should be in a state of equilibrium, which in turn is obtained upon addition of the catalyst catalyzing the conversion between the first and the second mutually convertible compounds. Upon establishment of a state of equilibrium, the concentration of one of the first or the second compounds is measured.

In yet another embodiment, the step of determining the equilibrium concentrations comprises the addition to the liquid phase of the first and/or the second compound(s) in (a) predetermined amount(s), and optionally computing the equilibrium concentrations therefrom.

The reference solution according to the invention may be used for calibration or quality control of a sensor, which is sensitive to at least one of the first and second compounds or a parameter derived therefrom. The reference solutions may be stored at a reduced temperature at which the catalyst degradation is minimized. At this temperature, the equilibrium between the mutually convertible compounds may be shifted compared to their equilibrium at the operating temperature of the reference solution.

To establish a state of equilibrium at a conditioning temperature, the reference solution is conditioned in the temperature range of 18-32° C., preferably 20-25° C., prior to calibration or quality control of the sensor. The conditioning temperature may correspond to the operating temperature.

The reference solution may be conditioned for a period in the range of 0.1-8 hours, preferably 0.1-3 hours.

Conditioning may be done by leaving the solution at the given temperature, e.g., at ambient temperature, or by heating or cooling the reference solution by means of a heating or cooling element. Conditioning may also be done on the kit providing the reference solution. Where the reference solution is stored at a temperature near the operating temperature, the need for conditioning may be eliminated.

EXAMPLES

The following describes an embodiment of the invention in which the first and the second compounds are creatinine and creatine, respectively, and the catalyst is an enzyme which catalyzes the conversion between creatinine and creatine.

Creatinine, 2-imino-1-methylimidazolidin-4-one, is a degradation product of creatine, α-methyl-guanidoacetic acid, which plays an important role in the storage and transmission of phosphate-bond energy in the muscles of vertebrates. The compounds are mutually convertible into each other, as shown in (1):

(1)

The level of creatinine in blood and urine provides useful information regarding renal function. Whereas the normal concentration of creatinine in blood is in the range 20-80 μM for children and 50-130 μM for adults, concentrations may reach as high as 1500 μM for persons with renal failure or uremic syndrome.

For the determination of creatinine levels, enzymatic assays based on the hydrolysis of creatinine to creatine have been developed. In one such assay, see e.g., International Published Patent Application WO 02/14533, creatinine is converted into creatine, which in turn is converted to sarcosine, which is oxidized to glycine, formaldehyde and hydrogen peroxide. The concentration of hydrogen peroxide is then determined amperometrically. This sensor system is a dual electrode system comprising one electrode for the determination of the concentration of creatine, and another electrode for the determination of the total concentration of creatinine and creatine. The assay allows determination of the concentration of creatinine from the difference between the total concentration of creatinine and creatine and the concentration of creatine.

The uncatalyzed conversion between creatinine and creatine is slow but significant. The rate constant for the first order conversion of creatinine into creatine at 25° C. at pH=7.4 is $2.4 \times 10^{-3}$ $d^{-1}$. For the reverse reaction it is $1.4 \times 10^{-3}$ $d^{-1}$. At 40° C., the rate constants are $10.1 \times 10^{-3}$ $d^{-1}$ and $8.5 \times 10^{-3}$ $d^{-1}$, respectively. At 6° C., the rate constants are $2.2 \times 10^{-4}$ $d^{-1}$ and $0.8 \times 10^{-4}$ $d^{-1}$, respectively. As such, the time required for uncatalyzed conversion may be counted in days, months or even in years.

The catalyzing enzyme for the creatinine-creatine system may be creatinine amidohydrolase, which is also referred to as creatininase. This enzyme, e.g., as supplied by Roche Diagnostics, has an enzymatic activity of approx. 80 IU/mg, and it may be added to the reference solution in a concentration in the range of 1-12 IU/ml.

The total concentration of creatinine and creatine in the reference solution may be in the range of 50-2,000 μM, corresponding to ambient temperature concentrations of creatinine in the range of approx. 20-750 μM and of creatine in the range of approx. 30-1,250 μM. This range of creatinine concentrations covers the reference range of children and adults of 20-80 μM and 50-130 μM, respectively, as well the onset levels of renal insufficiency of approx. 200 μM and of renal failure of approx. 500 μM, and thus represents a broad range of practical use.

With reference to the exemplary embodiment shown in FIG. 1, the container 100, made from 1.5 mm polyethylene, for example, comprises two separate compartments, 110 and 120. The larger compartment 110 has a capacity of 250 ml and holds 200 ml of a pH=7.4 buffer of HEPES. The smaller compartment 120 holds a mixture of 5.7 mg of creatinine, 11.2 mg of creatine and 1500 IU of creatinine amidohydrolase. The smaller compartment 120 is separated from the larger compartment 110 by a 60 μm polyester membrane 130.

When a moderate manual pressure is exerted on the outer surface of the smaller compartment 120, the membrane 130 is displaced into the larger compartment 110, and creatinine, creatine and creatinine amidohydrolase are transferred to the buffer solution in the larger compartment 110. The solution is ready for use after being conditioned for 3 h at the operating temperature of 25° C. The concentrations of creatinine and creatine in the reference solution prepared in this manner are 250 μM and 425 μM, respectively.

In a comparison study, three containers, denoted A, B and C, were prepared as described above, and the concentrations of creatinine and creatine measured by HPLC. The containers were then stored at 6° C. for one year. Following the one year storage, container (A) was stored for another 14 days at 6° C., and subsequently conditioned for 3 hours at 25° C. Container (B) was stored for another 14 days at 25° C., and subsequently conditioned for 3 hours at 25° C. The third container (C) was stored for another 14 days at 40° C., and subsequently conditioned for 3 hours at 25° C.

The concentrations of creatinine and creatine in all three containers A, B and C were determined by HPLC and by a calibrated creatinine/creatine sensor of the type described above. The concentrations of creatinine and creatine were 250 µM and 425 µM, respectively, at 25° C., i.e., the concentrations were unchanged compared to the solutions as prepared.

COMPARATIVE EXAMPLE

For comparison, three additional containers, denoted A', B' and C', containing reference solutions with no enzyme, but otherwise identical to their counterparts A, B and C, were stored and conditioned under similar conditions as A, B and C.

Results

With the sample from container A' (6° C.), the concentrations of creatinine and creatine were 243 µM and 432 µM, respectively. With the sample from container B' (25° C.), the concentrations of creatinine and creatine were 243 µM and 432 µM, respectively. With the sample from container C' (40° C.), the concentrations of creatinine and creatine were 260 µM and 415 µM, respectively. This comparative study demonstrates that with solutions containing no enzyme, the relative creatinine/creatine compositions may deviate significantly from their equilibrium compositions, i.e., at 25° C.

Figure 2:
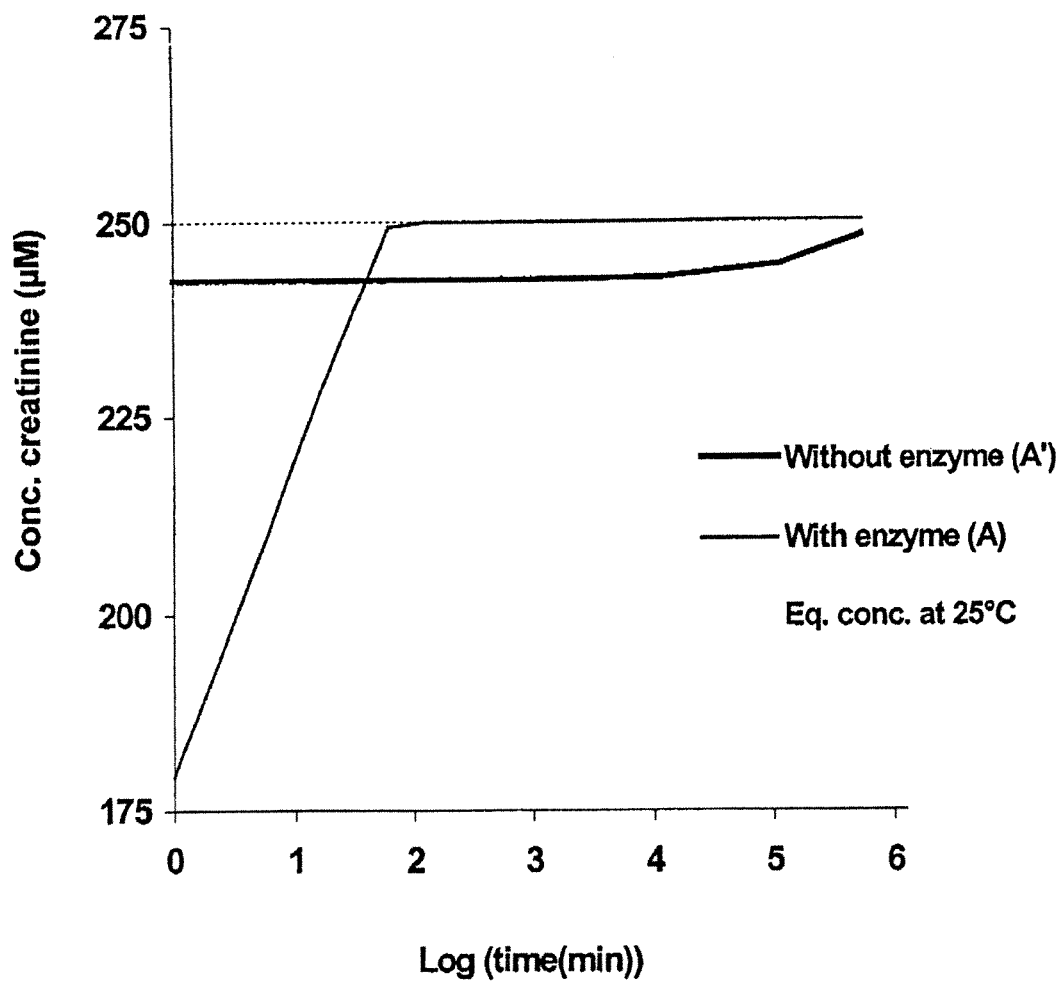
FIG. 2 shows comparable data for the concentration of creatinine vs. time upon conditioning of reference solutions with and without enzyme present.

FIG. 2 shows the creatinine concentration vs. time for samples from containers A and A' during extended conditioning at 25° C. for a period of 1 year. During this conditioning period, the creatinine concentrations of A and A' were determined at t=0 min., t=15 min., t=60 min, t=120 min., t=1,000 min. (approx. 17 hours), t=10,000 min. (approx. 7 days), t=100,000 min. (approx. 70 days) and at t=525,600 min. (one year) as described above.

At t=0 min., i.e., at the onset of the conditioning period, the creatinine concentrations of A and A' were 179 µM and 243 µM, respectively. The concentration of A of 179 µM corresponds to the equilibrium concentration at the storage temperature of 6° C., i.e., from the onset of the conditioning period, this solution is in a state of equilibrium. This is not the case with the reference solution of A', which does not contain a catalyzing enzyme. During the one year storage at 6° C., the creatinine concentration of the solution in A' was reduced to 243 µM compared to an original concentration of 250 µM. It was, however, still well above the equilibrium level of 179 µM.

At t=120 min., the creatinine concentrations of A and A' were 250 µM and 243 µM, respectively. Thus, at t=120 min., the reference solution of A had already reached its state of equilibrium at 25° C., whereas the reference solution of A' was unchanged compared to the concentration at the onset of the conditioning period.

At t=525,600 min., i.e., after one year of conditioning, the creatinine concentrations of A and A' were 250 µM and 248 µM, respectively. Thus, even after this extended period of conditioning, the reference solution of A' had not yet reached a state of equilibrium.

This comparative study demonstrates that the presence of a catalyzing enzyme may significantly reduce the conditioning period required for establishment of equilibrium, and that in the absence of a catalyzing enzyme, establishment of equilibrium may not be feasible at all.

The claimed invention is:

1. A method of calibrating a sensor for determining creatinine and creatine levels in a sample, the method comprising the steps of:
    exposing the sensor to a reference solution comprising
        creatinine and creatine in equilibrium in a liquid phase, wherein the concentrations of the creatinine and the creatine in the solution are the equilibrium concentrations of the creatinine and the creatine; and
        at least one catalyst dissolved in the solution, which catalyzes the conversion between the creatinine and the creatine,
    determining the sensor response to the concentrations of the creatinine and the creatine in the reference solution; and
    adjusting the sensor accordingly.

2. The method of claim 1, wherein the at least one catalyst is creatinine amidohydrolase.

3. The method of claim 1, further comprising preparing the reference solution by:
    adding the creatinine and creatine to the liquid phase in a predetermined amount.

4. The method of claim 1, further comprising preparing the reference solution by:
    adding to the liquid phase the creatinine and the creatine and the at least one catalyst; and
    determining the equilibrium concentrations of the creatinine and the creatine at a selected temperature.

5. The method of claim 4, wherein the step of determining the equilibrium concentrations comprises:
    measuring the total concentrations of the creatinine and the creatine; and
    computing the equilibrium concentrations therefrom.

6. The method of claim 4, wherein the step of determining the equilibrium concentrations comprises:
    measuring the concentrations of each of the creatinine and the creatine; and
    computing the equilibrium concentrations therefrom.

7. The method of claim 4, wherein the step of determining the equilibrium concentrations comprises:
    allowing establishment of the equilibrium concentrations of the creatinine and the creatine after addition of the at least one catalyst;
    measuring the equilibrium concentration of one of the creatinine and the creatine; and
    computing the equilibrium concentrations therefrom.

8. A method of performing quality control of a sensor comprising:
    exposing the sensor to a reference solution comprising
        creatinine and creatine in equilibrium in a liquid phase, wherein the concentrations of the creatinine and the creatine in the solution are the equilibrium concentrations of the creatinine and the creatine; and
        at least one catalyst dissolved in the solution which catalyzes the conversion between creatinine and creatine,
    determining the sensor response to the concentrations of the creatinine and the creatine in the reference solution; and
    adjusting the sensor accordingly
    if the determined concentrations are outside a predetermined acceptance range.

9. The method of claim 8, wherein the at least one catalyst is creatinine amidohydrolase.

10. The method of claim 8, further comprising preparing the reference solution by adding the creatinine and creatine to the liquid phase in a predetermined amount.

11. The method of claim 8, further comprising preparing the reference solution by adding to the liquid phase the creatinine and the creatine and the at least one catalyst; and determining the equilibrium concentrations of the creatinine and the creatine at a selected temperature.

12. The method of claim 11, wherein the step of determining the equilibrium concentrations comprises:
   measuring the total concentrations of the creatinine and the creatine; and
   computing the equilibrium concentrations therefrom.

13. The method of claim 11, wherein the step of determining the equilibrium concentrations comprises:
   measuring the concentrations of each of the creatinine and the creatine; and
   computing the equilibrium concentrations therefrom.

14. The method of claim 11, wherein the step of determining the equilibrium concentrations comprises:
   allowing establishment of the equilibrium concentrations of the creatinine and the creatine after addition of the at least one catalyst;
   measuring the equilibrium concentration of one of the creatinine and the creatine; and
   computing the equilibrium concentrations therefrom.

\* \* \* \* \*